United States Patent
Easter et al.

(10) Patent No.: US 9,254,161 B2
(45) Date of Patent: Feb. 9, 2016

(54) RADIOLUCENT HANDLE SYSTEM

(71) Applicants: Keith A. Easter, Kenosha, WI (US); Gao Hua, Fox Point, WI (US)

(72) Inventors: Keith A. Easter, Kenosha, WI (US); Gao Hua, Fox Point, WI (US)

( * ) Notice: Subject to any disclaimer, the term of this patent is extended or adjusted under 35 U.S.C. 154(b) by 323 days.

(21) Appl. No.: 13/913,588

(22) Filed: Jun. 10, 2013

(65) Prior Publication Data

US 2014/0364861 A1    Dec. 11, 2014

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/88* | (2006.01) | |
| *A61B 17/00* | (2006.01) | |

(52) U.S. Cl.
CPC ..... *A61B 17/8875* (2013.01); *A61B 2017/0046* (2013.01); *A61B 2017/0092* (2013.01)

(58) Field of Classification Search
CPC .................. A61B 17/8875; A61B 2017/0046; A61B 2017/0092
USPC ............................. 81/177.1, 177.2, 436, 489
See application file for complete search history.

(56) References Cited

U.S. PATENT DOCUMENTS

| | | | |
|---|---|---|---|
| 6,094,780 | A | 8/2000 | McGlothlin et al. |
| 7,981,116 | B2 | 7/2011 | Reeder, Jr. et al. |
| 2004/0097831 | A1 | 5/2004 | Bourne et al. |
| 2005/0085723 | A1 | 4/2005 | Huebner |
| 2007/0005076 | A1 | 1/2007 | Arnal |
| 2007/0027468 | A1 | 2/2007 | Wales et al. |
| 2007/0290399 | A1 * | 12/2007 | Easter et al. .................. 264/255 |

* cited by examiner

*Primary Examiner* — Christopher Beccia
*Assistant Examiner* — Diana S Jones
(74) *Attorney, Agent, or Firm* — Absolute Technology Law Group, LLC

(57) ABSTRACT

The present invention relates to the field of medical devices, and more specifically to a radiolucent surgical handle system which utilizes properties of silicone and channel geometry to create a more responsive and stable medical instrument. Channel geometry is utilized to stabilize the outer silicone gripping layer, thus preventing axial, planar, lateral or angular movement of the silicone gripping layer under conditions of torque force during a surgical operation.

17 Claims, 5 Drawing Sheets

RADIOLUCENT HANDLE SYSTEM

FIELD OF INVENTION

The present invention relates to the field of medical devices, and more specifically to a surgical instrument handle which is radiolucent, highly stable and responsive under torque force due to the utilization of novel channel geometry to stabilize the outer silicone gripping layer.

TERMS OF ART

As used herein, the term "dovetailed tab" means a protruding structure integrally formed from silicone which is t-shaped or y-shaped.

As used herein, the term "dovetailed channel" means a channel having adjacent recesses which are adapted to form t-shaped or y-shaped silicone structures.

BACKGROUND

X-ray imaging is used during orthopedic surgery and other medical procedures to guide surgeons in real time, and also to verify completed procedures while the patient is still on the operating table. Surgeons use specialized medical tools to complete their work, and at times these tools cannot be removed from the field of x-rays. Typical tools have stainless steel or other metal in the handles that can block x-rays and thus affect surgical outcomes. It is desirable to have tools with handles that are radiolucent so they do not block x-rays.

Radiolucent materials are known in the art. Silicone is a highly effective material for surgical handles because it is lightweight and provides a sure grip, and it is also radiolucent. However, silicone must be supported by a strong inner frame structure, usually comprised of a material that is not radiolucent such as stainless steel.

Attempts have been made to design inner skeletal frame structures for surgical tool handles using radiolucent materials. For example, U.S. Patent Application No. 2007/0290399 A1 (Easter) discloses a surgical tool handle with an outer silicone gripping layer and a radiolucent inner skeletal support structure which directs the flow of silicone though channels in the frame to form spines with overlapping edges that serve as interlocking components.

It is known in the art that surgical tools must be stable and must avoid the problem of lateral movement of the silicone over the inner skeletal frame. Attempts in the art to manufacture radiolucent tool handles have focused on design of inner skeletal frames.

It is desirable have a design which maximizes the stability of a torque resistant radiolucent handle which optimizes and varies the geometry of the inner skeletal frame of the tool to prevent the composite layers from slipping against each other and achieves the strength of metal tools.

SUMMARY OF THE INVENTION

The present invention is a torque-resistant radiolucent handle surgical tool with optimized radiating silicone flow channels that utilize novel geometric features to prevent axial, planar, lateral or angular movement of the silicone gripping layer under conditions of torque force during a surgical operation.

The outer silicone gripping layer is bound to the inner skeletal frame by a plurality of angled silicone tabs, rather than spines known in the art. The channel geometry utilizes novel segmented or spiral configurations with unique structural features, including t-shaped and y-shaped dove tail structures which provide increased stability over edged spines. The degree of the outer channel retaining angles may be varied to optimize resistance to torque force without disrupting the flow of silicone. The ratio of channel depth to channel floor, the space between channels and the depth of the dovetail are improved geometric structures which improve the stability of the tool.

DETAILED DESCRIPTION OF INVENTION

Figure 1:
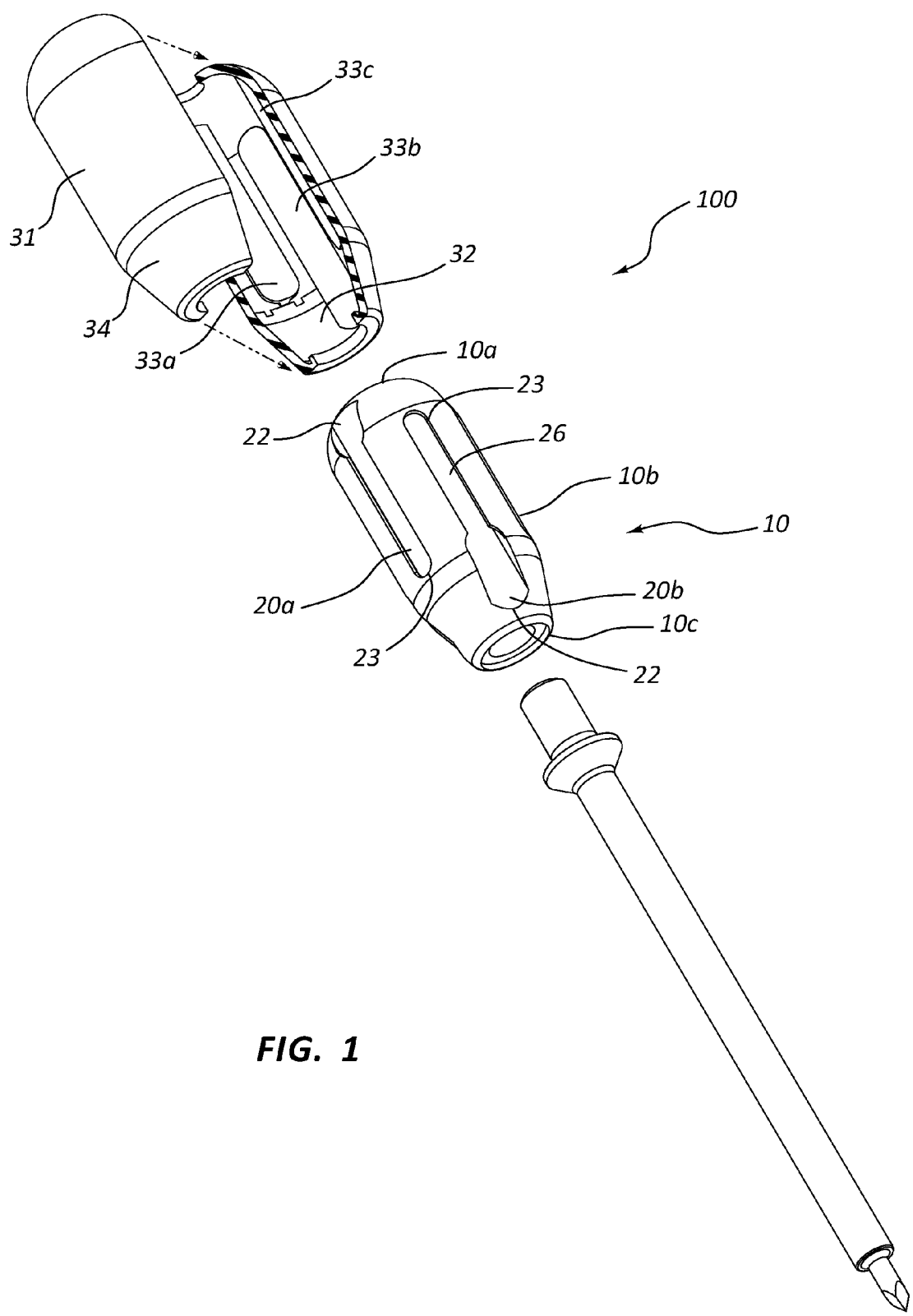
FIG. 1 is an exploded view of an exemplary embodiment of a radiolucent handle system illustrating an inner skeletal frame and outer silicone gripping layer in use with a surgical tool.

For the purpose of promoting an understanding of the present invention, references are made in the text to exemplary embodiments of a geometrically coalesced instrument handle, only some of which are described herein. It should be understood that no limitations on the scope of the invention are intended by describing these exemplary embodiments. One of ordinary skill in the art will readily appreciate that alternate but functionally equivalent structures and materials may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

FIG. 1 is an exploded view of an exemplary embodiment of a radiolucent handle apparatus 100 for use as a surgical tool, which includes an outer silicone gripping layer 31 and an inner skeletal frame 10 that acts as an inner stabilizing component.

FIG. 1 illustrates an asymmetrical inner skeletal frame 10 with a flattened angular end 10a, a continuous cylindrical center portion 10b, and a curved flattened end 10c. The exemplary embodiment of an outer silicone gripping layer 31 shown in FIG. 1 has an inner surface 32 and an outer surface 34.

Also illustrated in FIG. 1 are radiating silicone flow channels 20a and 20b. In the exemplary embodiment shown in FIG. 1 each radiating silicone flow channel has an open channel end 22 and a terminating channel end 23. FIG. 1 also depicts an inner channel floor 26.

In the embodiment shown in FIG. 1, radiating silicone flow channels 20a and 20b are alternately placed so that each of the radiating silicone flow channels 20a and 20b has a terminating channel end 23 and an open channel end 22 placed opposite of the terminating channel ends 23 and the open channel ends 22 of the radiating silicone flow channels 20a and 20b adjacent to it.

Figure 2A:
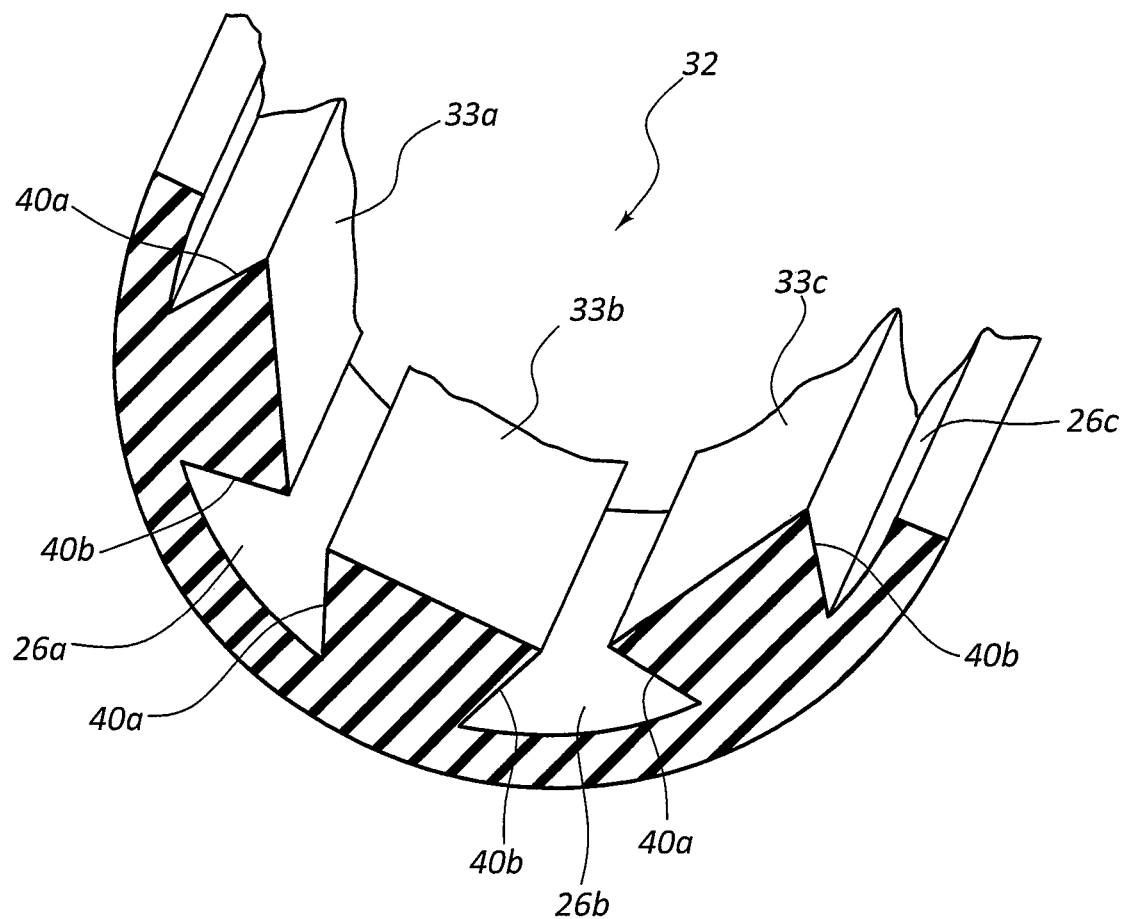
FIGS. 2a and 2b are cross-sectional views which illustrates the contours the inner surface of an outer silicone gripping layer with integrated angled dovetailed silicone tabs.
Figure 2B:
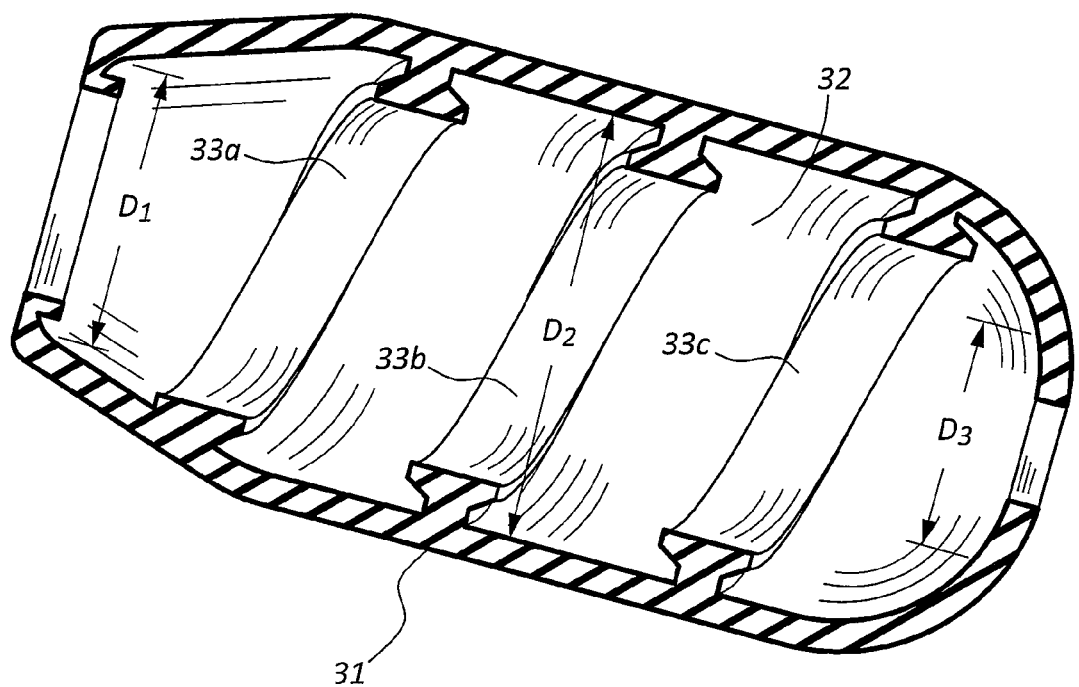

FIGS. 2a and 2b illustrate cross-sectional views of two exemplary embodiments of a radiolucent handle apparatus 100.

FIG. 2a illustrates the contours of the inner surface of a silicone layer with integrally formed angled dovetailed silicone tabs 33a-33c protruding above the inner surface 32 of the outer silicone gripping layer 31. Angled dovetailed silicone tabs 33a-33c are disposed of outer channel retaining angles 40a, 40b of 90 to 150 degrees.

In various embodiments of the apparatus, inner surface 32 may have more or fewer angled dovetailed silicone tabs 33a-33c to withstand torque force and to be adapted to the contours and dimensions of a particular surgical tool. Outer channel retaining angles 40a, 40b may be varied to accommodate torque force characteristics. Additionally, the length and width dimensions of inner channel floor 26 may be varied proportionally to accommodate the torque force, dimensions and mechanical characteristics of a specific surgical tool to which the radiolucent handle apparatus 100 may be attached.

The shape of the angled dovetailed silicone tabs 33a-33c is critical to stabilizing the outer silicone gripping layer 31 and securing it to inner skeletal frame 10 so that there is no axial, planar, lateral or angular movement of the silicone gripping layer under conditions of torque force during a surgical operation.

FIG. 2b illustrates an outer silicone gripping layer 31 comprised of an asymmetrical tubular body having an inner surface 32 and an outer surface 34. Outer silicone gripping layer 31 includes a flattened angular end having a first inner diameter $D_1$, a continuous cylindrical center having a second inner diameter $D_2$, and a curved flattened end having a third inner diameter $D_3$. In the embodiment shown, D1 is greater than D3.

FIG. 2b illustrates an embodiment in which radiating silicone flow channels 20a-20c are contiguously arranged in a continuous spiral configuration.

Figure 3A:
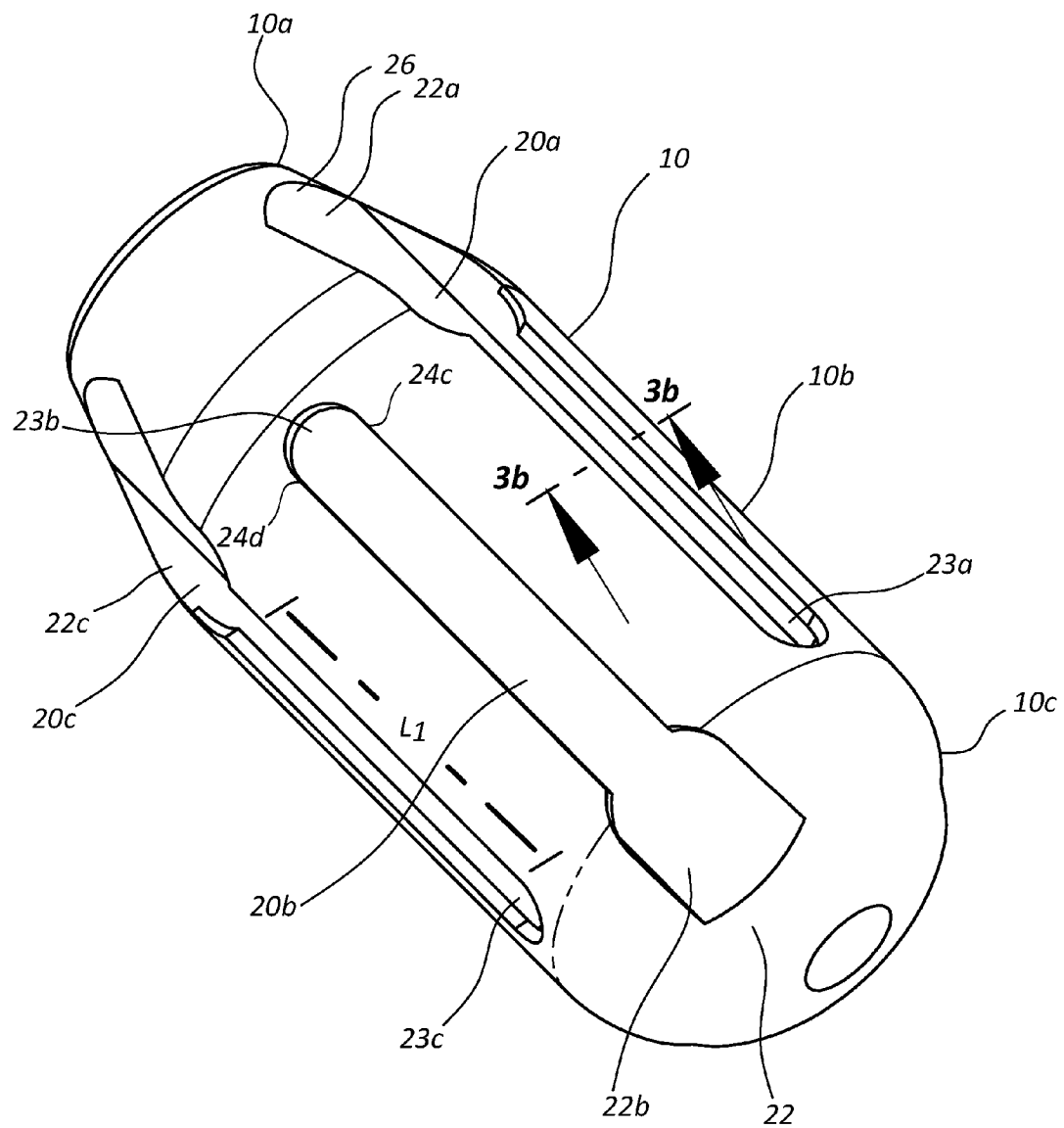
FIG. 3a illustrates an exemplary embodiment of an inner skeletal frame for a radiolucent handle system.

FIG. 3a illustrates an exemplary embodiment of an inner skeletal frame 10 for a radiolucent handle system 100 illustrating a configuration of radiating silicone flow channels 20a-20c. The inner skeletal frame 10 is a primary stabilizing component that has a flattened angular end 10a, a continuous cylindrical center portion 10b, and a curved flattened end 10c.

In the embodiment shown in FIG. 3a, the radiating silicone flow channels 20a-20c are alternately placed so that each radiating silicone flow channel 20a and 20b has a terminating channel end 23 and an open channel end 22 placed opposite of the terminating channel ends 23 and open channel ends of the radiating silicone flow channels 20a and 20b adjacent to it.

In the embodiment shown in FIG. 3a, the width of each of the terminating ends 23a-23c is greater than the width of the channel opening 22a-22c. Each terminating end is bounded by an angled opposing dovetailed channel side 24c and 24d (not shown). Each of the opposing sides create a force to oppose movement of the angled dovetailed silicone tabs 33a and 33b (not shown).

As shown in FIG. 3a, each radiating silicone flow channel further includes elongated inner channel floor 26, two dovetailed angled side surfaces 28a, 28b, and two outer channel retaining portions 42a, 42b. Each dovetailed angled surface and outer channel retaining portion encloses a dovetailed recess 29a, 29b that receives a corresponding angled dovetailed silicone tab 33a, 33b (not shown).

Figure 3B:
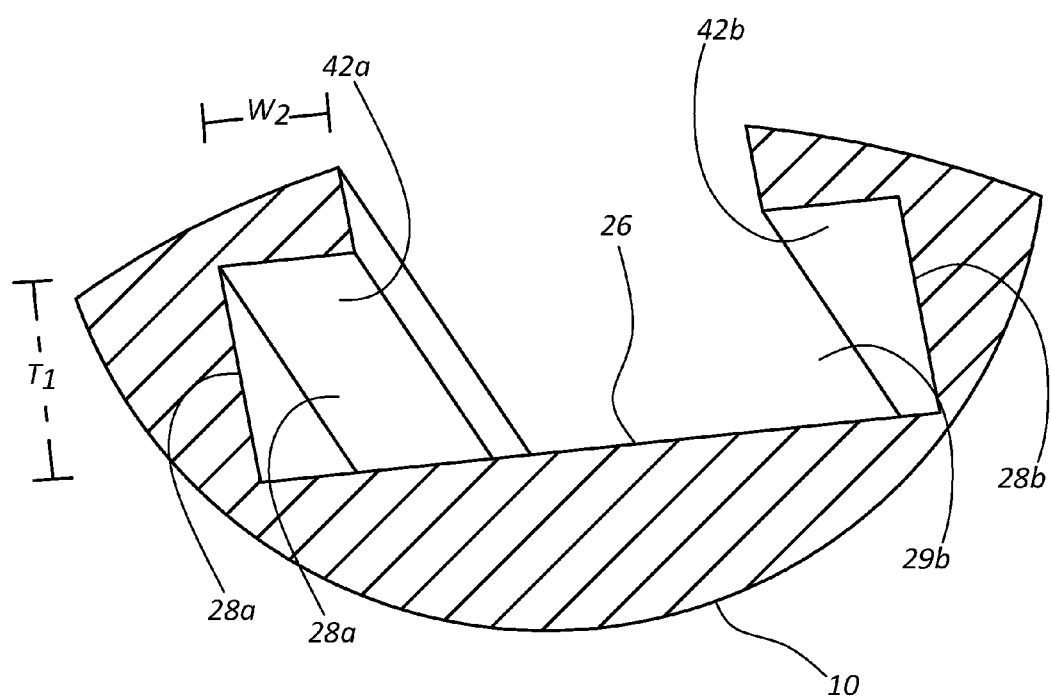
FIG. 3b illustrates a sectional view of an exemplary embodiment of an inner skeletal frame for a radiolucent handle system illustrating a configuration of radiating silicone flow channels.

FIG. 3b illustrates a sectional view of a radiolucent handle system 100 with inner stabilizing geometric components, including inner skeletal frame 10 and outer silicone gripping layer 31, which utilize principles of highly stabilizing channel geometry.

In the embodiment shown in FIG. 3b, outer channel retaining angles 40a, 40b are angled, perpendicular or substantially perpendicular to inner channel floor 26 and partially enclose said channel and provide a silicone retention barrier.

In the the exemplary embodiments shown, the ratio of non-channel surface area to channel space is less than 30 percent.

In these exemplary embodiments, the ratio of the height of angled dovetailed silicone tab 33 to the inner channel floor 26 to the width of the elongated portion of the tab is 40 to 50 percent.

What is claimed is:

1. A torque-resistant radiolucent silicone handle apparatus comprised of an:
   outer silicone gripping layer having an inner surface and an outer surface, wherein said inner surface includes a plurality of integrally formed angled dovetailed silicone tabs;
   and an inner skeletal frame comprised of an asymmetrical tubular body having an inner surface and an outer surface and wherein said asymmetrical tubular body further includes:
   a flattened angular end having diameter $D_1$;
   a continuous cylindrical center having diameter $D_2$;
   a curved flattened end having diameter $D_3$; and
   a plurality of radiating silicone flow channels, wherein each of said radiating silicone flow channels are contiguously arranged in a continuous spiral configuration.

2. The apparatus of claim 1 wherein each of said plurality of radiating silicone flow channels has a terminating channel end and an open channel end.

3. The apparatus of claim 2 wherein a width of each of said terminating channel end is greater than a width of each of said open channel end.

4. The apparatus of claim 2 wherein each terminating channel end is bounded by an angle formed of opposing dovetailed channel sides.

5. The apparatus of claim 4 wherein each of said opposing dovetailed channel sides creates a force to oppose movement of angled dovetailed silicone tabs.

6. The apparatus of claim 2 wherein said plurality of radiating silicone flow channels are placed so that each terminal channel end is placed opposite to said terminal channel end of the adjacent radiating silicone flow channel.

7. The apparatus of claim 6 wherein said dovetailed angled side surfaces are disposed at outer channel retaining angles of 90 to 150 degrees.

8. The apparatus of claim 6 wherein each of said dovetailed recesses comprise a dovetailed angled side surface and an outer channel retaining portion having a length $L_1$ and a depth $W_2$.

9. The apparatus of claim 6 wherein the inner channel floor extends beyond the outer end of dovetailed angled side surfaces at each open channel end.

10. The apparatus of claim 1 wherein said continuous spiral configuration further includes continuous spiral inner channel floors, at least two continuous spiral dovetailed angled side surfaces and at least two continuous spiral dovetailed recesses.

11. The apparatus of claim 10 wherein each said dovetailed recesses has a thickness $T_2$.

12. The apparatus of claim 1 wherein each of said radiating silicone flow channels has an inner channel floor, at least two dovetailed angled side surfaces having a thickness $T_1$ and at least two dovetailed recesses at the upper end of each of said dovetailed angled side surfaces.

13. The apparatus of claim 1 wherein each of said angled dovetailed silicone tabs has an outer channel retaining angle of 90 to 150 degrees.

14. The apparatus of claim 1 which further includes three or more pairs of radiating silicone flow channels.

15. The apparatus of claim 1 wherein $D_1$ is greater than $D_3$.

16. The apparatus of claim 1 wherein a ratio of non-channel surface area to channel space is less than 30 percent.

17. The apparatus of claim 1 wherein a ratio of a height of the angled dovetailed silicone tab above the inner channel floor to a width of an elongated portion of the tab is 40 to 50 percent of said height.

* * * * *